United States Patent [19]

Golias

[11] 4,341,635

[45] Jul. 27, 1982

[54] MICROCHROMATOGRAPHIC COLUMN AND METHOD

[75] Inventor: Tipton Golias, Beaumont, Tex.

[73] Assignee: Helena Laboratories Corporation, Beaumont, Tex.

[21] Appl. No.: 216,888

[22] Filed: Dec. 16, 1980

[51] Int. Cl.³ .......................................... B01D 15/08
[52] U.S. Cl. ............................. 210/656; 210/198.2
[58] Field of Search ....................... 210/656, 659, 198.2

[56] References Cited

U.S. PATENT DOCUMENTS

| | | | |
|---|---|---|---|
| 3,250,395 | 5/1966 | Blume | 210/198.2 |
| 3,922,223 | 11/1979 | Burkhartsmeier | 210/198.2 |
| 4,112,743 | 9/1978 | Mowery, Jr. | 210/659 X |

FOREIGN PATENT DOCUMENTS 52-51993  4/1977  Japan ................ 210/198.2

*Primary Examiner*—John Adee

*Attorney, Agent, or Firm*—Cullen, Sloman, Cantor, Grauer, Scott & Rutherford

[57] ABSTRACT

A liquid microchromatographic column having a tubular reservoir portion receiving the fluid solution to be separated and discharging into a barrel portion containing finely divided ion exchange particles for separating the solution. A cap having an inlet port is received in sealed relation on the reservoir portion open end. The inlet port of the cap has a smooth generally cylindrical internal surface for receiving the discharge tip of a microsyringe or other pressure source, in sealed relation. The chromatographic method of this invention then includes introducing the fluid solution to be separated and an eluting solution into the reservoir. The discharge tip of a microsyringe is then inserted into the inlet port of the cap and the plunger of the syringe is depressed to increase the pressure in the reservoir and create a pressure drop across the ion exchange particles, substantially reducing the time required for chromatographic separation.

8 Claims, 2 Drawing Figures

MICROCHROMATOGRAPHIC COLUMN AND METHOD

FIELD OF THE INVENTION

Chromatography is a method of separating and analyzing small quantities of substances by passing a solution containing the substances through a column of finely divided particles which selectively adsorb the constituents of the solution. Initially, chromatography relied upon physical separation of the substances in one or more sharply defined colored bands. More recently, ion exchange chromatographic methods permit separation and quantitation of charged molecules, such as proteins and hemoglobins, making the procedure very useful in medical research and clinical evaluation.

Ion exchange resins are now commercially available in various pH ranges to selectively adsorb various molecules. The commercial ion exchange resins are a preparation of cellulose resin or other ion exchange resin particles which attract negatively charged molecules. Proteins, such as hemoglobins, contain many positive and negative charges due to the ionizing properties of the component amino acids. In anion exchange chromatography, the pH levels are controlled to cause different molecules to possess different net negative charges. The negatively charged molecules are attracted to the positively charged cellulose and bind accordingly.

Following binding, the molecules are selectively removed from the resin by altering the pH or ionic strength of the eluting solutions. The eluting solutions are used to selectively strip one component or molecule from the ion exchange resin column, leaving the remainder. This procedure can be used several times to separate a number of differently charged molecules.

Ion exchange columns and eluting solutions are also commercially available in kit form for separation and quantitation of various molecules, including hemoglobin $A_{1c}$, hemoglobin $A_2$, Vanillylamandelic Acid (VMA), Creatine Phosphokinase (CPK) MB, Lactic Dehydrogenase ($LDH_{1,2}$) and the molecular sieving and desalting chromatography used for Carcinoembryonic Antigen (CEA) assays. A more detailed description of the microchromatographic method of separation and quantitation of glycosylated hemoglobin is given hereinbelow as an example of the method and column of this invention, however it will be understood that the microchromatographic column and method of this invention may be used for any similar procedure.

A microchromatographic column generally includes a cylindrical barrel portion, which contains the ion exchange particles, and which discharges into a reduced diameter discharge tip portion, which is capped prior to use. The commercial microchromatographic columns generally include an enlarged reservoir portion, which serves as a funnel to receive the solution to be separated and which discharges into the barrel portion. The ion exchange particles are generally supported on a filter disc located between the barrel portion and the reduced diameter discharge tip portion. Microchromatographic columns of this type are available from the Assignee of the instant application, Helena Laboratories Corporation.

The glycosylated hemoglobin test is based upon the clinical determination that three minor components of norman human hemoglobin, $HbA_{1a}$, $HbA_{1b}$ and $HbA_{1c}$, exhibit faster chromatographic mobilities than the main band of hemoglobin, HbA. Those minor components are collectively referred to as glycosylated hemoglobins, G-Hb, and differ from the major component HbA only by having a carbohydrate moiety attached to the N-terminal valine of the beta globin chain. It has now been discovered that the concentration of glycosylated hemoglobins, particularly $HbA_{1c}$, is related to the average blood sugar level in humans. A microchromatographic technique has been developed whereby the glycosylated hemoglobins may be quantitatively determined rapidly and simply in a liquid microchromatographic column. As described above, the negatively charged resin exhibits an affinity for positively charged molecules. At selective ion strength and pH, the glycosylated hemoglobins are less positively charged than hemoglobin A. Therefore, the glycosylated hemoglobins bind to the negatively charged resin less tightly than hemoglobin A. With the application of a first developing buffer, the glycosylated hemoglobins are eluted, while the other hemoglobin components are retained by the ion exchange resin. This fraction may then be compared to a total fraction or a second developing eluting buffer is used to elute the remaining hemoglobins to determine the percentage of glycosylated hemoglobins to total hemoglobins.

U.S. Pat. Nos. 4,142,855, 4,142,857 and 4,142,858, which are incorporated herein by reference, describe a chromatographic method of determining the concentration of glycosylated hemoglobins in blood and a microcolumn used for such tests. The microchromatographic column and method of this invention is an improvement upon the methods described in the referenced patents. However, as described hereinabove, the microchromatographic column and method of this invention are not limited to the determination of glycosylated hemoglobins.

The liquid chromatographic column and method described in the above referenced patents rely upon gravity for elution, requiring sixty to ninety minutes for the first elution and twenty to thirty minutes for the second elution. More recent improvements in microchromatographic columns by the assignee of this invention and others has limited the elution time to about twenty minutes, or about ten minutes for each elution. There is also an existing form of chromatography which utilizes high pressure to drive the eluting solution or developer. This method is called high pressure liquid chromatography or HPLC. The HPLC method however requires expensive equipment, costing several thousands of dollars, and operates under high pressures, which are not suitable for conventional microchromatographic columns. The need therefore remains for a simple, relatively inexpensive microchromatographic method which may be performed in seconds, rather than twenty to sixty minutes. The microchromatographic column and method of this invention achieves both purposes.

SUMMARY OF THE INVENTION

The liquid microchromatographic column of this invention includes a tubular barrel portion preferably terminating in a reduced diameter discharge tip as described above. The fluid solution to be separated is received in a tubular reservoir portion which discharges into the barrel portion and an open end. As described, the barrel portion contains the finely divided ion exchange particles for separating the fluid solution which is received in the reservoir portion. A cap is sealingly received on the open end of the tubular reservoir portion. The cap includes an inlet port having a smooth generally cylindrical internal surface for receiving the cylindrical discharge tip of a conventional microsyringe or similar pressure source, in sealed relation. The microsyringe may thus be used to increase the pressure in the reservoir portion of the column and form a pressure drop across the ion exchange particles, substantially reducing the time required for chromatographic separation.

In the preferred embodiment, the cap is generally cup-shaped having an internally threaded lip portion and the cap is threadably received on the tubular open end of the reservoir portion. The cap preferably includes a sealing means, such as a sealing disc, to seal the reservoir upon receipt of the microsyringe. A microsyringe is normally plastic and the cylindrical internal surface of the inlet port is also preferably plastic to form a good seal between the discharge tip of the syringe and the reservoir of the microcolumn. A conventional microsyringe may be utilized in the method of this invention, including a barrel portion and a plunger. Depression of the syringe plunger, with the syringe discharge tip in the column inlet port increases the pressure in the reservoir to form a pressure drop across the ion exchange particles, as described above.

The method of this invention therefore includes introducing the fluid solution to be separated and an eluting solution into the column, through the open end of the reservoir. The discharge tip of a microsyringe is then inserted into the inlet port of the cap and the plunger of the syringe is depressed to create a pressure drop across the ion exchange particles, as described above. This method reduces the time for chromatographic separation from about ten to thirty minutes per elution to about ten seconds. Where two or more elutions are required, the time is reduced from about twenty to sixty minutes, to about twenty seconds. The time savings can be of tremendous advantage for certain assays. For example, the method of this invention will allow a doctor to evaluate data during the patient's office visit, rather than at a later time, which may be extremely important in immediate patient care.

Other advantages and meritorious features of the present invention will be more fully understood from the following detailed description of the microchromatographic column and method of this invention and the drawings, a brief description of which follows.

DETAILED DESCRIPTION OF THE PREFERRED EMBODIMENTS AND METHOD

Figure 1:
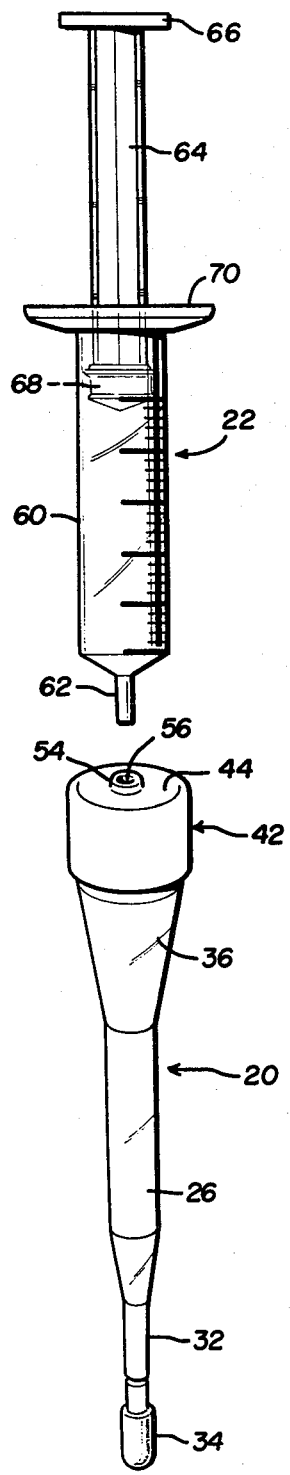
FIG. 1 is a side elevation of the microchromatographic column of this invention with a conventional microsyringe.

As described above, the microchromatographic column 20 of this invention is adapted to separate fluid solutions under the pressure generated by a microsyringe 22, reducing the time of elution by a factor of about sixty. The disclosed microchromatographic column includes a cylindrical barrel portion 26 containing ion exchange resin particles 28. As described above, the particles are adapted to separate molecules in the column on the basis of charge. In the preferred embodiment, the column bed comprises a suspension of particles of a microgranular ion exchange cellulose. In the glycosylated hemoglobin test described above, the column comprises granular cation exchange resin equilibrated in phosphate buffer to pH 6.70 with 0.065% KCN. Further details of a suitable column are described in the above referenced U.S. patents, the disclosure of which is incorporated herein. In the disclosed microchromatographic column, the particles are supported on a suitable filter disc 30 located between the cylindrical discharge portion 26 and the reduced diameter discharge tip portion 32. A suitable filter disc is a high density polyethylene disc of the Ziegler type. A cap 34 is received on the end of the discharge tip to seal the tip prior to use. In the disclosed embodiment of the column, the fluid solution to be separated is received in the enlarged reservoir portion 36, which discharges into the barrel portion 26 and contains the supernatant 38, following filtration.

In the microchromatographic column of this invention, the reservoir is closed by an end cap 42 including an end portion 44 and a cylindrical lip portion 46. In the disclosed embodiment, the lip portion is internally threaded at 48 to be threadably received on the externally threaded end portion 50 of the reservoir. A sealing disc 52 is preferably received between the end of the tubular reservoir portion 36 and the end portion 46 of the cap. The cap may be formed of any suitable plastic including polyethylene or polystyrene. Any suitable sealing material may be utilized, including paper, cork and plastic materials. The end portion of the cap includes an inlet port 54 having a smooth generally cylindrical internal surface 56 to receive the discharge tip of a microsyringe or a similar pressure source, such as a rubber bulb, in sealed relation, as described hereinbelow. The internal surface of the inlet port may be slightly conical to form a tighter seal with the microsyringe. The disclosed microsyringe 22 is conventional and may be purchased commercially from a number of suppliers. The disclosed microsyringe includes a barrel portion 60 which is calibrated by volume. A typical microsyringe of this type has a volume of five cubic centimeters. The barrel portion terminates in a reduced diameter cylindrical discharge tip 62 having a smooth exterior surface. A plunger 64 is received in the barrel portion. A typical plunger is cruciform shaped having a flat end portion 66 and a head portion 68. In the disclosed embodiment, the head portion includes a soft polyurethane head having a plurality of radially extending cylindrical flange portions which sealingly engage the internal cylindrical surface of the barrel portion and force air or fluid from the barrel portion through the discharge tip 62. The disclosed embodiment of the microsyringe also includes a pair of opposed radially extending finger grip portions 70, which are integral with the barrel portion.

The chromatographic separation method of this invention comprises introducing the fluid solution to be separated and an eluting solution into the reservoir 36 of the microchromatographic column 20. The solution is then received in the cylindrical barrel portion 26 into the finely divided ion exchange particles or granules 28. As described above, the ion exchange resin is negatively charged and will covalently couple to small positively charged molecules. In the glycosylated hemoglobin test described above, the hemoglobins will adhere to the negatively charged ion exchange particles to be selectively stripped by the eluting solutions. In the hemoglobin test, the pH or ionic strength of the first eluting solution is chosen to selectively remove the glycosylated hemoglobins, as described in the above referenced patents. The sample and the eluting solutions may be received through the open end of the reservoir, with the cap removed or through the inlet port 54 of the end cap, using a micropipette. In the test described in the above referenced patents, the solutions flow through the ion exchange cellulose particles 28, solely under the influence of gravity. As stated therein, this procedure takes sixty to ninety minutes.

Figure 2:
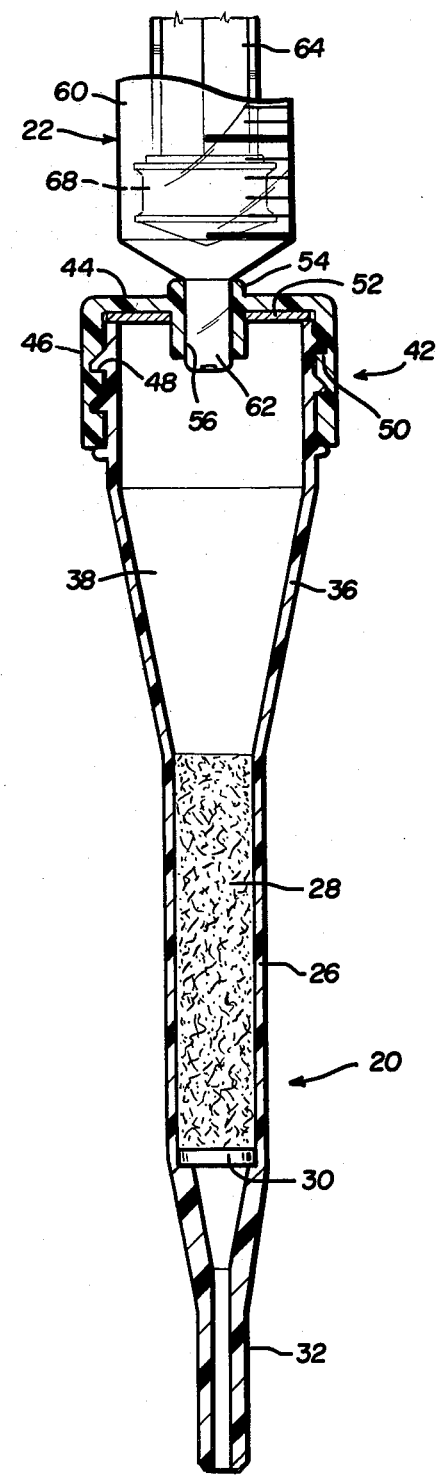
FIG. 2 is a cross-sectional side view of the microchromatographic column of FIG. 1 with a partial cross-sectional view of the microsyringe in the operating position.

In the method of this invention, the time required for chromatographic separation is substantially reduced by using the pressure generated by the microsyringe 22. As shown in FIG. 2, the discharge tip 62 of the microsyringe is inserted into the inlet port 54 of the end cap 42. The smooth cylindrical surface 62 of the discharge tip is received within the smooth internal generally cylindrical surface 56 of the inlet port in sealed relation and the plunger 64 is depressed, forcing air through the discharge tip of the syringe and increasing the pressure in the reservoir 36. This creates a pressure drop across the ion exchange cellulose particles 28 and reduces the time required for chromatographic separation to about ten seconds. Where a second eluting solution is utilized, the procedure is repeated, including introducing the second eluting solution into the reservoir 36 and inserting the discharge tip 62 of the microsyringe into the inlet port 54 of the end cap and depressing the plunger 64 of the microsyringe to create a pressure drop across the ion exchange cellulose particles 28.

The following Examples illustrate the time savings using the microsyringe assisted chromatographic test of this invention, wherein a pressure column created by the microsyringe is compared to a conventional gravity column of the improved type referred to hereinabove. It will be noted that the total elution time in each of the Examples is twenty seconds, compared to a total elution time for the gravity column of twenty minutes. For example, the time savings of a microsyringe assisted chromatographic test for hemoglobin $A_{1c}$ will allow a doctor to evaluate the data during the patient's office visit, rather than at a later time. This could be very important in adjusting the patient's blood sugar level.

EXAMPLE 1

Established Range: 6.0–8.0
Mean Value: 7.0

Data Section

| GLYCOSYLATED VALUES | |
|---|---|
| Pressure (Microsyringe) Column | Control (Gravity) Column |
| Col. #1–6.5 | Col. #1–7.2 |
| Col. #2–7.0 | Col. #2–7.3 |
| Col. #3–6.8 | Col. #3–6.7 |
| Col. #4–6.9 | |
| Col. #5–6.7 | |
| Mean - 6.8 | Mean - 7.0 |
| Standard Deviation - .19 | Standard Deviation - .32 |
| Coefficient of Variation - 2.8% | Coefficient of Variation - 4.5% |
| Elution Time: 2 times | Elution Time: 2 times |
| 10 seconds = 20 seconds | 10 minutes = 20 minutes |

EXAMPLE 2

Established Range: 5.2–7.2
Mean Value: 6.2

Data Section

| GLYCOSYLATED VALUES | |
|---|---|
| Pressure (Microsyringe) Column | Control (Gravity) Column |
| Col. #1–6.3 | Col. #1–6.3 |
| Col. #2–5.8 | Col. #2–6.5 |
| Col. #3–6.3 | Col. #3–6.5 |
| Col. #4–6.1 | |
| Col. #5–5.9 | |
| Col. #6–6.1 | |
| Mean - 6.1 | Mean - 6.4 |
| Standard Deviation - .20 | Standard Deviation - .12 |
| Coefficient of Variation - 3.4% | Coefficient of Variation - 1.8% |
| Elution Time: 2 times | Elution Time: 2 times |
| 10 seconds = 20 seconds | 10 minutes = 20 minutes |

EXAMPLE 3

Data Section

| GLYCOSYLATED VALUES | |
|---|---|
| Pressure (Microsyringe) Column | Control (Gravity) Column |
| Col. #1–8.4 | Col. #1–7.9 |
| Col. #2–8.0 | Col. #2–8.0 |
| Col. #3–7.9 | Col. #3–8.4 |
| Col. #4–8.1 | |
| Col. #5–8.1 | |
| Col. #6–7.5 | |
| Col. #7–7.7 | |
| Col. #8–7.5 | |
| Mean - 7.9 | Mean - 8.1 |
| Standard Deviation - .32 | Standard Deviation - .26 |
| Coefficient of Varation - 4.0% | Coefficient of Varation - 3.3 |
| Elution Time: 2 times | Elution Time: 2 times |
| 10 seconds = 20 seconds | 10 minutes = 20 minutes |

The "glycosylated values" listed for each chromatographic column tested in each of the above Examples are the percentages of glycosylated hemoglobin of the total hemoglobins. The method is briefly described hereinabove and described in more detail in the publications of the assignee and the above referenced U.S. patents. The determination is made using a standard laboratory spectrophotometer. The following formula was used to calculate the percentage of glycosylated hemoglobin for each column, using the method described above:

$$\frac{\text{Optical Density of the Fast Fraction Column}}{5 \text{ (Optical Density of Total Fraction Column)}} \times 100 = \text{percentage glycosylated hemoglobin}$$

The optical density or absorbance of the contents of the fast fraction column, which is eluted with the first eluting solution and the total fraction collected with the second eluting solution was measured at a wave length of 415 nanometers. The dilution factor of 5 in the formulation is based upon the difference in volume between the total fraction of 15 milliliters and 3 milliliters of the fast fraction. More information regarding the method of calculation may be obtained from the published literature of the Assignee regarding the present gravity microchromatographic method used for quantitation of glycosylated hemoglobin.

As described above and established in the above Examples, the method of this invention substantially reduces the time required for chromatographic separation and quantitation of various solutions utilizing an ionic microchromatographic column and method. The Examples establish that the method of this invention is as accurate as the conventional gravity separation, however the time is reduced from twenty minutes to twenty seconds. This is a very important improvement in chromatographic separation, particularly for patient clinical evaluations, where time may be of the essence. It will be understood that various modifications may be made to the microchromatographic column of this invention which has been adapted for use with a conventional microsyringe, which substantially reduces the cost of the apparatus and method of this invention.

I claim:

1. A liquid microchromatographic column having a tubular barrel portion terminating in a reduced diameter discharge tip, a tubular reservoir portion discharging into said barrel portion having an open end for receiving the liquid solution to be separated, said barrel portion containing finely divided ion exchange particles for separating the fluid solution received in said reservoir portion, and a cap received on said reservoir portion open end in sealed relation, said cap having an end portion including an integral generally cylindrical portion extending through said cap end portion on opposite sides of said end portion having an inlet port extending therethrough discharging into said reservoir portion, said inlet port having an elongated conical smooth internal surface closely receiving the cylindrical discharge tip of a hand operated pressure means in sealed relation for increasing the pressure in said reservoir and forming a pressure drop across said ion exchange particles, thereby reducing the time required for chromatographic separation.

2. The liquid microchromatographic column defined in claim 1, characterized in that said cap is cup-shaped having an internally threaded lip portion threadably received on said open end of said tubular reservoir portion, said cap including a sealing means sealing the communication between said inlet port of said cap and said reservoir portion of said column.

3. The liquid microchromatographic column defined in claim 1, characterized in that said cap is cup-shaped having an open end received over said reservoir open end and said sealing means comprising a sealing disc located between said reservoir open end and said end portion of said cap.

4. A liquid microchromatographic column having a tubular barrel portion terminating in a reduced diameter discharge tip, a tubular reservoir portion discharging into said barrel portion having an open end for receiving the fluid solution to be separated, said barrel portion containing finely divided ion exchange particles supported on a filter disc, said particles separating the fluid solution received in said reservoir portion, and a cap received on said reservoir portion open end in sealed relation, said cap being cup-shaped having an end portion and an internally threaded lip portion threadably received on said reservoir portion open end, and said cap end portion having an integral generally cylindrical portion extending through said cap end portion on opposite sides of said end portion having an inlet port extending through said cylindrical portion communicating with said reservoir portion, said inlet port having an elongated smooth generally cylindrical internal surface receiving the cylindrical discharge tip of a microsyringe in sealed relation for increasing the pressure in said reservoir and forming a pressure drop across said ion exchange particles and forcing fluid through said ion exchange particles, thereby reducing the time required for chromatographic separation.

5. The liquid microchromatographic column defined in claim 4, characterized in that said cap includes a sealing disc located between said cap end portion and said open end of said tubular reservoir portion.

6. A method of separating fluid solutions in a chromatographic column, said column having an open end for receiving the fluid solution, finely divided ion exchange particles supported in said column for separating the fluid solution and a cap received on said column open end in sealed relation having an elongated smooth, generally cylindrical inlet port, said method comprising:
   a. introducing the fluid solution to be separated and an elutant into said column, through said open end, and
   b. inserting the discharge tip of a hand operated pressure means into said cap inlet port in sealed relation and creating a pressure drop across said ion exchange particles by compressing said hand operated pressure means to force said eluent through said ion exchange particles, thereby reducing the time required for chromatographic separation.

7. The method of claim 6, wherein said pressure means is a syringe having a plunger, including depressing said plunger to create said pressure drop.

8. A method of separating a fluid solution in a microchromatographic column, said column having a tubular reservoir having an open end for receiving the solution to be separated, said reservoir discharging into a barrel portion of said column having finely divided ion exchange particles supported therein, and a cap closing said reservoir end portion in sealed relation, said cap having an inlet port communicating with said reservoir, the chromatographic method of separation comprising:
   a. introducing the fluid solution to be separated and a first elutant into said reservoir, through said open end,
   b. inserting the discharge tip of a microsyringe having a plunger into said cap inlet port in sealed relation with said inlet port and depressing said plunger to increase the pressure in said reservoir and create a pressure drop across said ion exchange particles, and
   c. introducing a second fluid elutant into said reservoir, through said open end and inserting the discharge tip of said microsyringe into said cap inlet port and depressing said syringe plunger to create a pressure drop across said ion exchange particles to force said elutant through said ion exchange particles.

* * * * *